(12) United States Patent
Weibrecht et al.

(10) Patent No.: US 9,248,313 B2
(45) Date of Patent: Feb. 2, 2016

(54) MARKER ADAPTED NORMAL TISSUE COMPLICATION PROBABILITY

(75) Inventors: Martin Weibrecht, Aachen (DE); Jens Christoph Georgi, Aachen (DE); Carolina M. Ribbing, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 707 days.

(21) Appl. No.: 13/256,767

(22) PCT Filed: Feb. 18, 2010

(86) PCT No.: PCT/IB2010/050732
§ 371 (c)(1),
(2), (4) Date: Sep. 15, 2011

(87) PCT Pub. No.: WO2010/109357
PCT Pub. Date: Sep. 30, 2010

(65) Prior Publication Data
US 2012/0004492 A1  Jan. 5, 2012

Related U.S. Application Data

(60) Provisional application No. 61/240,685, filed on Sep. 9, 2009, provisional application No. 61/230,839, filed on Aug. 3, 2009, provisional application No. 61/163,983, filed on Mar. 27, 2009.

(51) Int. Cl.
*A61N 5/00* (2006.01)
*A61N 5/10* (2006.01)
*G06Q 50/22* (2012.01)

(52) U.S. Cl.
CPC ............... *A61N 5/103* (2013.01); *G06Q 50/22* (2013.01); *A61N 5/1038* (2013.01)

(58) Field of Classification Search
CPC ........... A61N 5/00; A61N 5/10; A61N 5/103; A61N 5/1038; A61N 5/1039
USPC ........................................ 600/1–8, 410, 427
See application file for complete search history.

(56) References Cited

U.S. PATENT DOCUMENTS

| 7,073,129 B1 | 7/2006 | Robarts et al. |
| 2004/0254448 A1 | 12/2004 | Amies et al. |

(Continued)

FOREIGN PATENT DOCUMENTS

| RU | 2140081 C1 | 10/1999 |
| RU | 2268474 C1 | 1/2006 |

(Continued)

OTHER PUBLICATIONS

Meteora Buffa, et al., "Incorporating Biologic Measurements (SF2, CFE) into a Tumor Control Probability Model Increases Their Prognostic Significance: A Study in Cervical Carcinoma Treated with Radiation Therapy", Int. J. Radiation Oncology Biol. Phys. vol. 50, No. 5, pp. 1113-1122 (2001).

(Continued)

*Primary Examiner* — Christine H Matthews

(57) ABSTRACT

A therapy system includes a diagnostic image scanner (12) that acquires a diagnostic image of a target region to be treated. A planning processor (70) is configured to generate a patient specific adaptive radiation therapy plan based on patient specific biomarkers before and during therapy. A first set of patient specific biomarkers is determined then used for the determination of a first normal tissue complication probability (NTCP) model and a first tumor control probability (TCP) model. A radiation therapy device (40) administers a first dose of radiation to the target region with a protocol based on the first NTCP model and the first TCP model. A second set of patient specific biomarkers is determined. A relationship between the first set and second set of patient specific biomarkers is used to determine a second NTCP model and a second TCP model. The radiation therapy device (40) administers a second dose of radiation to the target region with a protocol based on the second NTCP model and second TCP model.

16 Claims, 6 Drawing Sheets

(56) References Cited

U.S. PATENT DOCUMENTS

| | | | |
|---|---|---|---|
| 2006/0128792 A1* | 6/2006 | Lee | 514/453 |
| 2007/0043286 A1 | 2/2007 | Lu et al. | |
| 2007/0276777 A1 | 11/2007 | Krishnan et al. | |
| 2009/0093713 A1* | 4/2009 | Hyde et al. | 600/427 |

FOREIGN PATENT DOCUMENTS

| | | |
|---|---|---|
| RU | 2285445 C2 | 10/2006 |
| WO | 2008016795 A1 | 2/2008 |

OTHER PUBLICATIONS

Castella, et al., "Telomere Length Modulates Human Radiation Sensitivity in vitro", Toxicology Letters 172 (2007) 29-36.

Chi, et al., "Hypoxia Responses: How Different Cells and Tumors React to Oxygen Shortage", PLoS Medicine, Mar. 2006, V. 3, No. 3.

Hedman, et al. "Comparison of Prediced and Clinical Response to Radiotherapy: A Radiobiology Modeling Study", Acta Oncologica, 48(4), 2009, pp. 584-590.

Le, et al., "Galectin-1: A Link Between Tumor Hypoxia and Tumor Immune Privilege", J. Clint Oncol, V. 23, No. 35, Dec. 10, 2005, pp. 8932-8941.

Levegruen, et al., "Fitting Tumor Control Probability Models to Biopsy Outcome After Three-Dimensional Conformal Radiation Therapy of Prostate Cancer: Pitfalls in Deducing Radiobiologic Parameters for Tumors from Clinical Data", Int. J. Radiation Oncology Biol. Phys., V. 51, N. 4, pp. 1064-1080 (2001).

MacKay, et al. "The Modelled Benefits of Individualizing Radiotherapy Patients' Dose Using Cellular Radiosensitivity Assays with Inherent Variability", Radiotherapy and Oncology 50 (1999) 67-75.

Peeters, et al. "Rectal Bleeding, Fecal Incontinence, and High Stool Frequency After Conformal Radiotherapy for Prostate Cancer: Normal Tissue Complication Probability Modeling", Int. J. Radiation Oncology Biol. Phys., vol. 66, No. 1, pp. 11-19, 2006.

Sanchez-Nieto, et al., "Individualization of Dose Prescription Based on Normal-Tissue, Dose-Volume and Radiosensitivity Data", Int. J. Radiation Oncology Biol Phys. V. 49, N. 2, pp. 487-499 (2001).

Rickhey, M., et al.; Optimizing Tumor Control Probability, Assuming a Heterogeneous Distribution of Radiobiological Properties for Gioblastoma; 2008; I. J. Radiation Oncology Biology Physics; 72(1)abstract.

Smith, W., et al. "A Decision Aid for Intensity-Modulated Radiation-Therapy Plan Selection in Prostate Cancer Based on a Prognostic Bayesian Network and a Markov Model", Artif. Intell. Med., 46(2) Jun. 2009, pp. 119-130.

Sohn, M. et al. "The Incidence of Late Rectal Bleeding in High-Dose Conformal Radiotherapy of Prostate Cancer using EUD- and Dose-Volume Based NTCP Models", Int. J. Radiat Oncol Biol Phys Mar. 15, 2007; 67(4) 1066-1073.

Stevens, et al., "Radiosensitivity Can Be Predicted by DNA-End Binding Complex Analysis", I.J. Radiation Oncology Biology, Physics, [133] V. 57, No. 2, Supplement 2003.

Van Der Wel, et al., "Increased Tumor Control Probability (TCP) and Radiation Dose Escalation by FDG-PET Planning of Patients with N2/N3 M0 Non-Small Cell Lung Cancer (NSCLC): A Modeling Study", [784] Poster Session S236, Sep. 24, 2003.

* cited by examiner

MARKER ADAPTED NORMAL TISSUE COMPLICATION PROBABILITY

CROSS REFERENCE TO RELATED APPLICATIONS

This application claims the benefit of U.S. provisional application Ser. No. 61/163,983 filed Mar. 27, 2009 and U.S. provisional application Ser. No. 61/230,839 filed Aug. 3, 2009 and U.S. provisional application Ser. No. 61/240,685 filed Sep. 9, 2009, all three of which are incorporated herein by reference.

The present invention relates to the therapy arts. It particularly relates to radiotherapy protocol planning of a subject using radiation to deliver controlled therapy to a target, and will be described with particular reference thereto.

Oncological radiotherapy is used for treating diseased tissue by applying ionizing radiation, e.g. high energy photons, protons, neutrons, electrons, heavy charged particles (e.g. carbon ions), or the like, to the diseased tissue or diseased region. Irradiated healthy tissue is usually damaged by the radiotherapy to at least some extent, and such radiation can produce detrimental side effects. To minimize damage to healthy tissue probability models are assigned to both diseased tissue and healthy tissue at risk. Examples of such models are the tumor control probability (TCP) and the normal tissue complication probability (NTCP). The TCP is a probabilistic disease model that gives an estimate of the local tumor control based on the tumor type and the specifics of the irradiation plan for that particular patient. The NTCP is a probabilistic model of radiation damage inflicted on healthy tissue resulting in side effects of a certain severity. The severity of radiation induced side effects is assessed by specific measures such as those provided in the European Organization for Research and Treatment of Cancer/Radiation Therapy Oncology Group (EORTC/RTOG) Acute Radiation Morbidity Scoring Criteria. Radiotherapy protocol planning is a trade-off between the TCP and the NTCP. The optimum tumor dose for a given radiotherapy plan maximizes the difference between the TCP and the NTCPs for the different risk organs. Hence, the NTCP is the dose-limiting factor.

NTCP models are sigmoid functions that relate the tumor dose to the probability of radiation damage in healthy tissue. A Gaussian function is a common model of probability density of the side effects. Other models apply different mathematical functions, e.g. Poisson statistical models or regression models. All approaches have in common that the dose-volume histogram (DVH) is evaluated for an average dose, usually in terms of an equivalent uniform dose EUD. The most widely used probability function is the Lyman EUD model which yields an error function that predicts 50% complication probability. The equation is as follows:

$$NTCP = \frac{1}{\sqrt{2\pi}} \int_{-\infty}^{t} \exp\left(\frac{-z^2}{s}\right) dx \quad (1a)$$

$$t = \frac{EUD - TD50}{m * TD50} \quad (1b)$$

$$EUD = \left(\sum_{i=1}^{N} D_i^{1/n} * \frac{V_i}{V_{tot}}\right)^n \quad (1c)$$

The parameter m denotes the slope of the sigmoid NTCP curve and the dose TD50 is defined by a 50% risk of complication. Equation 1c shows a common approach to calculate the $EUD_{NTCP}$ from the DVH. The parameter $D_i$ denotes the physical dose to a volume element where the total evaluated organ volume is $V_{tot}$. The EUD concept refers to different impacts of local radiation damage to the function of a whole organ. The spine, for instance, will not function even if only a small part is destroyed. The liver and lung, in contrast, may well function even if considerable parts are destroyed. The spine is an example of so-called serial organ; the lung and liver are so-called parallel organs. It is this property of an organ the EUD describes. In Equation 1c, the model parameter n is associated with the strength of the volume effects for the organ under consideration. If n approaches 1, the EUD equals the mean dose, i.e. the model describes a perfectly 'parallel' organ in which a large volume effect is present. If n approaches 0, the EUD becomes the maximum dose, i.e. the model describes a perfectly 'serial' organ in which no volume effect is present. As noted, various models for the mean dose used in the NTCP model have been reported.

NTCP models for various side effects in different organs are based on dose-volume histogram (DVH) data. They are determined by fitting the parameters of mathematical models of the NTCP to the actual side effect profiles, which have been determined in respective clinical studies. A rather comprehensive evaluation by Söhn et al. (Int. J. Rad. Oncol. Biol. Phys., 67 (2007), 1066-1073) showed that different NTCP models provided different qualities of estimating the probability of a specific side effect (in their case late rectal bleeding in prostate cancer radiotherapy). The analysis of this group, however, was purely based on distribution of radiation dose values (DVH). So far, hardly any clinical trials on NTCP have addressed individual risk profiles of patients. Consequently, current NTCP models represent population mean statistics.

However, radiosensitivity may vary significantly between individuals. For example, patients with a history of abdominal surgery generally have a lower tolerance to radiation than did patients without previous abdominal surgeries. Regarding the EUD, a dose-modifying factor of 1.1 for rectal bleeding and a factor of 2.5 for fecal incontinence has been determined by subdividing patient groups in those with history of abdominal surgery and those without. Ignoring such individual risk factors constitutes a systematic inaccuracy of the current NTCP models resulting in erroneous estimates of NTCP models for individuals. Overestimating the NTCP can lead to suboptimal dose delivery to the tumor and consequently reduces tumor control causing possible relapse for the patient. Underestimating the NTCP can result in severe side-effects that can prematurely halt the therapy.

TCP models are sigmoid functions that relate the tumor dose to the probability of tumor control. A Gaussian function is a common model of probability density of the side effects. Other models apply different mathematical functions, e.g. Poisson statistical models or regression models. All approaches have in common that the dose-volume histogram (DVH) is evaluated for an average dose, usually in terms of an equivalent uniform dose EUD. The most widely used probability function is the Lyman EUD model which yields an error function that predicts 50% complication probability. The equation is as follows:

$$TCP = \frac{1}{\sqrt{2\pi}} \int_{-\infty}^{t} \exp\left(\frac{-x^2}{2}\right) dx \quad (2a)$$

$$t = \frac{EUD - TD50}{m * TD50} \quad (2b)$$

-continued $$EUD = \left(\sum_{i=1}^{N} D_i^{1/n} * \frac{V_i}{V_{tot}}\right)^n \quad (2c)$$

The parameter m denotes the slope of the sigmoid TCP curve and the dose TD50 is defined by a 50% risk of complication. Equation 2c shows a common approach to calculate the $EUD_{TCP}$ from the DVH. The parameter $D_j$ denotes the physical dose to a volume element $V_j$, where the total evaluated organ volume is $V_{tot}$. The model parameter n is associated with the strength of the volume effects for the organ under consideration. If n approaches 1, the EUD equals the mean dose, i.e. the model describes a perfectly 'parallel' organ in which a large volume effect is present. If n approaches 0, the EUD becomes the maximum dose, i.e. the model describes a perfectly 'serial' organ in which no volume effect is present.

The present application provides a new and improved method and apparatus for adaptive radiotherapy protocol planning based on optimizing the normal tissue complication probability and tumor control probability according to individual patient specific markers which overcomes the above-referenced problems and others.

In accordance with one aspect, a method for generating a patient specific therapy plan includes generating an initial therapy plan. A therapy is administered according to the initial therapy plan. Either the initial therapy plan is based on the value of at least one biomarker, or the therapy plan is revised based on an updated value of at least one measure biomarker, and the therapy is re-administered according to the revised therapy plan.

In accordance with another aspect, a computer readable medium carries a program which controls a processor to perform the method for generating a patient specific therapy plan.

In accordance with another aspect, a planning process is programmed to control a therapy device to perform the method for generating a patient specific therapy plan.

In accordance with another aspect, a therapy system includes an image scanner, a therapy device, a graphic user interface, and a planning processor to perform the method for generating a patient specific therapy plan.

In accordance with another aspect, a processor is configured to generate an initial therapy plan based at least on one measured biomarker. The processor controls a therapy device to administer a based on the initial therapy plan.

In accordance with another aspect, a method of patient specific adaptive delivery of radiotherapy to a target region includes determining a first set of patient specific markers. Based on the first set of biomarkers, at least one of an NTCP model and a TCP model is determined then used to administer a dose of radiation to the target region. A second set of patient specific biomarkers is determined. A relationship between the first set and second set of patient specific biomarkers is the basis for at least one of a second NTCP model and second TCP model. A dose of radiation to the target region is administered based on at least one of the second NTCP and second TCP model.

One advantage is that patient specific adaptive delivery of radiotherapy increases the tumor control probability which reduces unnecessary relapse for the patient.

Another advantage is that patient specific adaptive delivery of radiotherapy reduces severe side-effects of radiation toxicity Another advantage is that radiation dose or treatment plan can be altered based on a patient's reaction to therapy.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
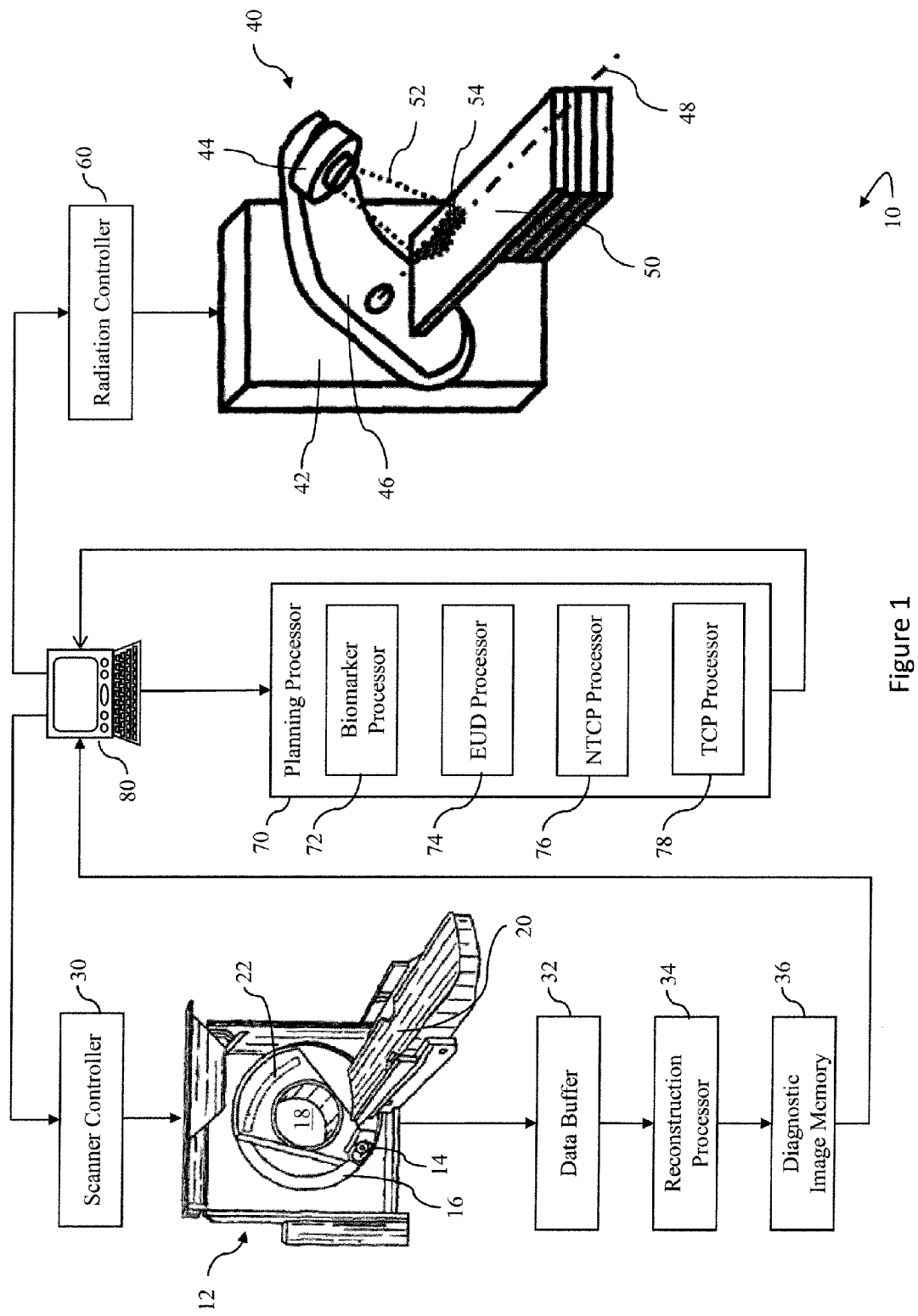
FIG. 1 is a diagrammatic illustration of an imaging and radiation therapy system.

With reference to FIG. 1, a therapy system 10, such as a radiation therapy system, includes a diagnostic imaging scanner 12 such as a computed tomography (CT) imaging scanner, an MRI scanner, or the like for obtaining diagnostic images for use in planning the radiation therapy protocol. The CT imaging scanner 12 includes an x-ray source 14 mounted on a rotating gantry 16. The x-ray source 14 produces x-rays passing through an examination region 18, where they interact with a target area of a subject (not shown) supported by a support 20 which positions the target area within the examination region 18. An x-ray detector array 22 is arranged to receive the x-ray beam after it passes through the examination region 18 where the x-rays interact with and are partially absorbed by the subject. The detected x-rays therefore include absorption information relating to the subject.

The CT scanner 12 is operated by a controller 30 to perform selected imaging sequences of a selected target area of the subject which is to be treated by radiotherapy. The imaging sequences acquire diagnostic imaging data of the target area. The diagnostic imaging data is stored in a data buffer 32. A reconstruction processor 34 reconstructs 3D image representations from the acquired imaging data, and the reconstructed image representations are stored in a diagnostic image memory 36.

The described diagnostic imaging system is exemplary only. Those skilled in the art will recognize that the CT scanner 12 is optionally replaced by other types of diagnostic imaging scanners, such as a magnetic resonance imaging (MRI) scanner, a positron emission tomography (PET) scanner, a single photon emission computed tomography (SPECT) scanner, or the like can be substituted for the CT scanner 12.

The diagnostic imaging apparatus 12 is separate from a therapy delivery system 40. The therapy delivery system can be an external radiotherapy delivery system or an internal radiotherapy delivery system, e.g. brachytherapy. Optionally, markers are applied to the subject prior to the diagnostic imaging, and remain in place for the subsequent radiotherapy to provide registration between the diagnostic images and the radiotherapy delivery. Other methods for spatial registering between diagnostic image acquisition and the radiotherapy are also contemplated, such as using intrinsic anatomical markers. It is also contemplated to integrate the diagnostic imaging scanner with the radiotherapy apparatus to reduce misregistration between the diagnostic imaging and the radiotherapy. Furthermore, other forms of therapy are also contemplated, e.g. ablation therapy, including thermal, chemical, HIFU, mechanical, or the like, or combined therapies such as radiation along with chemotherapy.

A radiation delivery system 40 includes a radiation delivery apparatus 42 which has a radiation source 44, such as a linear accelerator, focused x-ray, or the like mounted on a rotating gantry 46. The gantry 46 rotates or steps a radiation source 44 about an axis of rotation 48. A support 50 rigidly positions the subject with the target area exposed to an intensity-modulated radiation beam 52 produced by the radiation source 44. The support 50 positions and moves the subject while the gantry 46 rotates the radiation source 44 about the subject. The radiation beam 52 has a cross-sectional area 54 with an adjustable intensity and/or perimeter. The radiation beam 52 can be applied continuously or can be pulsed on and off during therapy. Optionally, a radiation detector system disposed on an opposite side of the patient from the source to monitor intensities of radiation traversing the patient. Data from the detector can be reconstructed into a low resolution projection image to monitor the alignment of the beam and the target and the dose. The radiation delivery system 40 is operated by a radiation controller 60 to perform selected radiation protocol as prescribed by a planning processor 70.

The planning processor 70 integrates individual patient specific information derived from a single or plurality of biomarkers into the calculation of the NTCP model and the TCP model using a patient specific calculation of an EUD for each model considering the biomarkers, for example telomere length which is associated with radiation sensitivity of cells. In one embodiment, by introducing a dose modifying factor into the EUD formulation (equation 1c), the biomarkers can be evaluated before and during therapy to derive a patient specific NTCP and TCP model. The adaptive EUD equations are as follows:

$$EUD = \left( \sum_{i=1}^{N} D_i^{1/n} * \frac{V_i}{V_{tot}} \right)^n \cdot g(M_1, \Delta M_1, M_2, \Delta M_2, \ldots) \quad (3a)$$

$$EUD = \left( \sum_{i=1}^{N} D_i^{1/n} * \frac{V_i}{V_{tot}} \right)^n \cdot g(M_1, \Delta M_1, M_2, \Delta M_2, \ldots) \quad (3b)$$

A patient specific dose modifying factor $g_{NTCP}$ and $g_{TCP}$ are scalar values that are evaluated based on an initial baseline and as well as changes to biomarker information M and L during therapy. For example, $g_{NTCP}=1.1$ for patients with a bleeding side effect; $g=2.5$ for a fecal incontinence side effect, and the like. A first baseline is a set of biomarker values associated with normal tissue that are derived before the therapy. The baseline values associated with normal tissue $M_k$ will be used to adapt the initial NTCP model before the therapy. Monitoring the biomarkers during therapy allows for optimizing the NTCP model for each patient based on specific reactions to the therapy. Therapy related changes $\Delta M_k$ are correlated to baseline values and then incorporated into the dose modifying factor $EUD_{NTCP}$. A second baseline is a set of biomarker values associated with cancerous tissue that are derived before the therapy. The baseline values associated with cancerous tissue $L_k$ will be used to adapt the initial TCP model before the therapy. Monitoring the biomarkers during therapy allows for optimizing the TCP model for each patient based on specific reactions to the therapy. Therapy related changes $\Delta L_k$ are correlated to baseline values and then incorporated into the dose modifying factor $EUD_{TCP}$. A biomarker processor 72 is responsible for initializing the dose modification factors based on the baseline values, $M_j$ and $L_k$, and optimizing the dose modifying factor during therapy based on the therapy related changes $\Delta M_k$ and $\Delta L_k$.

The marker values $M_k$ associated with normal tissue are of different kinds, e.g. in vitro test values, mass spectrometric protein signatures, anamnetic data, and patient history. The in vitro test values include cellular, proteomic and genetic origin such as, but not limited to, various cell counts, Hb, CRP, PSA, TNF-α, ferritin, transferrin, LDH, IL-6, hepcidin, creatinine, glucose, HbA1c, and telomere length. Anamnetic and patient history markers include previous abdominal surgery, hormonal or anticoagulantia medication, diabetes, age, and tumor growth related measures. Biomarkers not related to radiation toxicity are also contemplated such as biomarkers associated with various forms of ablation or chemotherapeutic agents.

The marker values $L_k$ associated with cancerous tissue include various kinds. Examples of biomarkers include PSA for prostate tumors and telomere length for cellular radiation sensitivity, i.e. shorter telomeres are associated with increased radiosensitivity. Genomic and proteomic biomarkers which reflect cellular radiosensitivity and repair capacities include analysis of DNA end binding complexes (DNA-EBCs). Examples of DNA-EBCs include measuring ATM, Ku70, DNA ligase III, Rpa32, Rpa14, DNA ligase IV, XRCC4, WRN, BLM, RAD51, and p53. Hypoxia is known to decrease tumor sensitivity to ionizing radiation. Molecular biomarkers which indicate tumor hypoxia includes HIF-1α, Galectin-1, CAP43, and NDRG1. Hypoxia biomarkers are also deduced from imaging procedures such as FMISO-PET and FAZA-PET which grade Oxygen partial pressure of individual image pixels.

Biomarkers describing various histologic outcomes include age, gender, medication, primary tumor site, previous treatment, individual patient wishes associated with personal perceptions, views on potential side-effects, and relapse risk. Other biomarkers describing histologic outcomes include histological tumor type, grade, stage, Gleason score, and cologenic assays such as clonogenic cell density, colony-forming efficiency (CFE), and radiosensitivity of clonogenic fibroblasts, e.g. the surviving fraction at 2 Gy ($SF_2$).

In another embodiment, a local correction factor $p_{TCP}$ is introduced into the $EUD_{TCP}$ formulation to modify the volume element $V_j$. The $EUD_{TCP}$ equation including the local correction factor is as follows:

$$EUD_{TCP} = \left( \sum_{j=1}^{N} D_j^{1/n} \frac{V_j \cdot p_{TCP}(Q_1, \Delta Q_1, Q_2, \Delta Q_2, \ldots)}{V_{tot}} \right)^n. \quad (3c)$$

$$g_{TCP}(L_1, \Delta L_1, L_2, \Delta L_2, \ldots)$$

The local correction factor $p_{TCP}$ is modifying by baseline biomarkers $Q_k$ and therapy related biomarkers $\Delta Q_k$ which are determined from imaging data. Biomarkers include swelling, perfusion, and interstitial fluid which can be determined with various imaging modalities such as magnetic resonance, x-ray, nuclear, ultrasound, optical, or the like.

The biomarker processor outputs the dose modifying factor to an input of an EUD processor 74 which processor updates the EUD calculation (equation 2) based on the optimized dose modifying factor. The EUD processor then outputs the optimized EUD calculation to an input of an NTCP processor 76 and a TCP processor 78, both of which output a respective optimized model (Equations 1a and 2a) to a console 80.

The console 80 includes a graphic user interface also includes a user input device which a clinician can use for controlling the scanner controller 30 or radiation controller 60 to select scanning sequences or protocols and treatment schemes or doses respectively. The console displays diagnostic images, segmentation tools, segmentation tools, graphs relating the TCP, NTCP, and the difference between the two models, and the like. The optimized NTCP and TCP models are used by a radiation oncologist to determine if the treatment plan is to be adjusted in terms of total dose applied, dose location, or replacing the treatment scheme with alternatives such as three-dimensional conformal radiotherapy, intensity modulated radiation therapy (IMRT), or another suitable fractionation scheme. Monitoring the biomarkers during therapy allows the NTCP and TCP models to be adapted to the specific patient.

Figure 2:
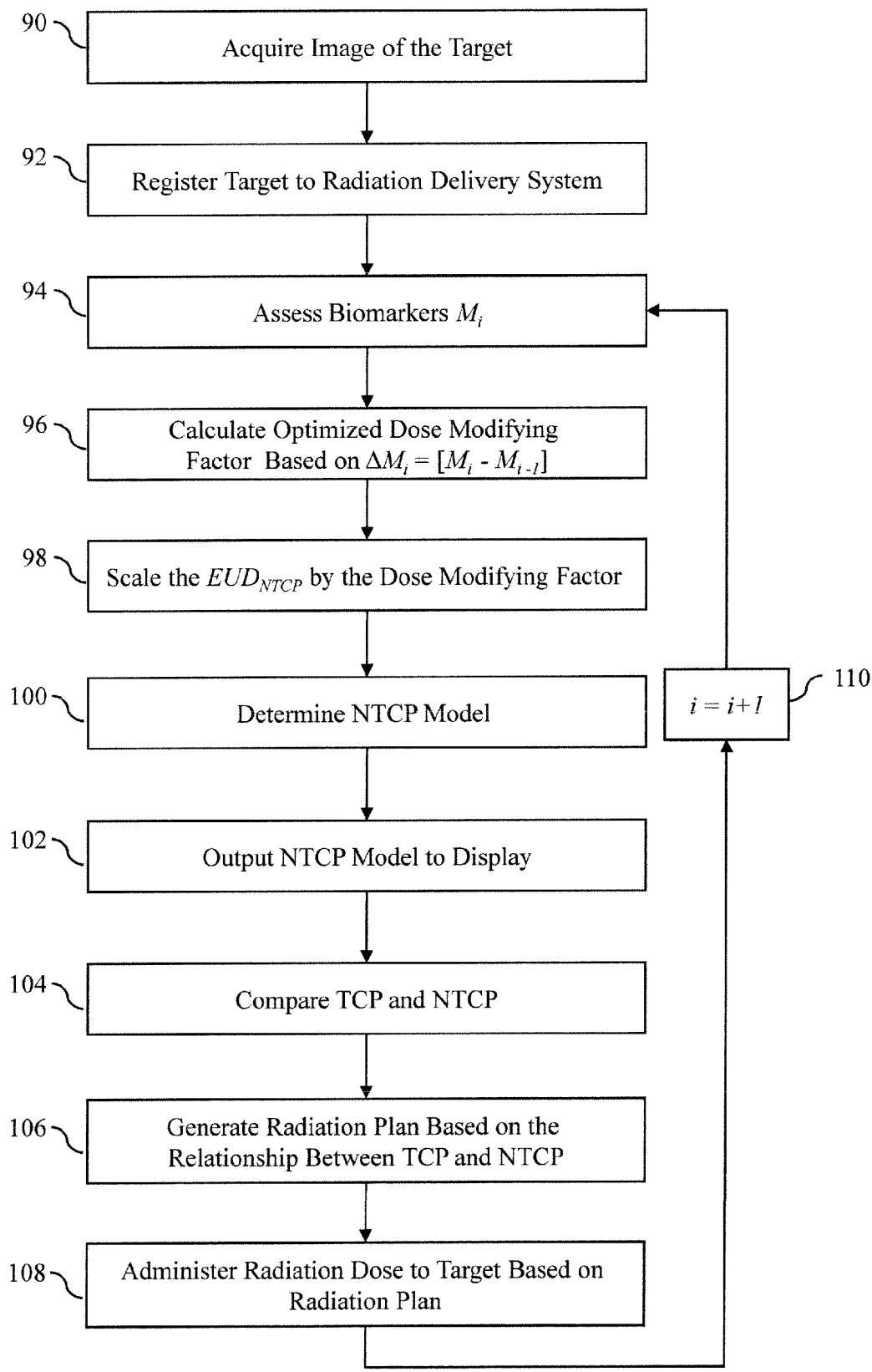
FIG. 2 is a flow diagram of an NTCP modeling process.

With continuing reference to FIG. 2, the NTCP model is refined in an iterative process in which the optimized dose modifying factor is set as the baseline in subsequent iterations. First a diagnostic image is acquired in step 90 using a CT, MRI, PET, SPECT, or another imaging modality. In step 92, the target is localized in a diagnostic image and then registered with the radiation delivery system 40 using any number of means such as active, passive, or intrinsic anatomical markers. Biomarkers are assessed in step 94. The biomarkers can be measured in vitro, based on patient history, anamnetic data, mass spectrometric protein signatures, and the like. A value is assigned to the individual biomarkers which are then used to calculate the optimized dose modifying factor in step 96. In the first iteration (for i=1), the dose modifying factor is based on an initial baseline because there is no prior dose modifying factor available. The dose modifying factor is then used to weight the $EUD_{NTCP}$ model in step 98 in response to the patient specific biomarkers from step 94. The patient specific $EUD_{NTCP}$ model is used in the calculation of the NTCP model in step 100. The NTCP model is then outputted 102 (FIGS. 4 and 5) on the graphic display of console 80 along with the TCP and the NTCP and the TCP are compared as in step 104. The radiation oncologist then determines if optimizations to the radiation therapy plan are needed in step 106. Such adjustments may include adjusting total dose applied, location of the dose, or changing the treatment regime to another such as IMRT, 3D conformal radiotherapy, or another fractionation scheme. In step 108, a radiation dose is administered to the target as prescribed by the optimized radiation plan. The optimized dose modifying factor is set as the baseline in step 110, and the optimization is reiterated until the radiation oncologist can determine that treatment is no longer needed.

Figure 3:
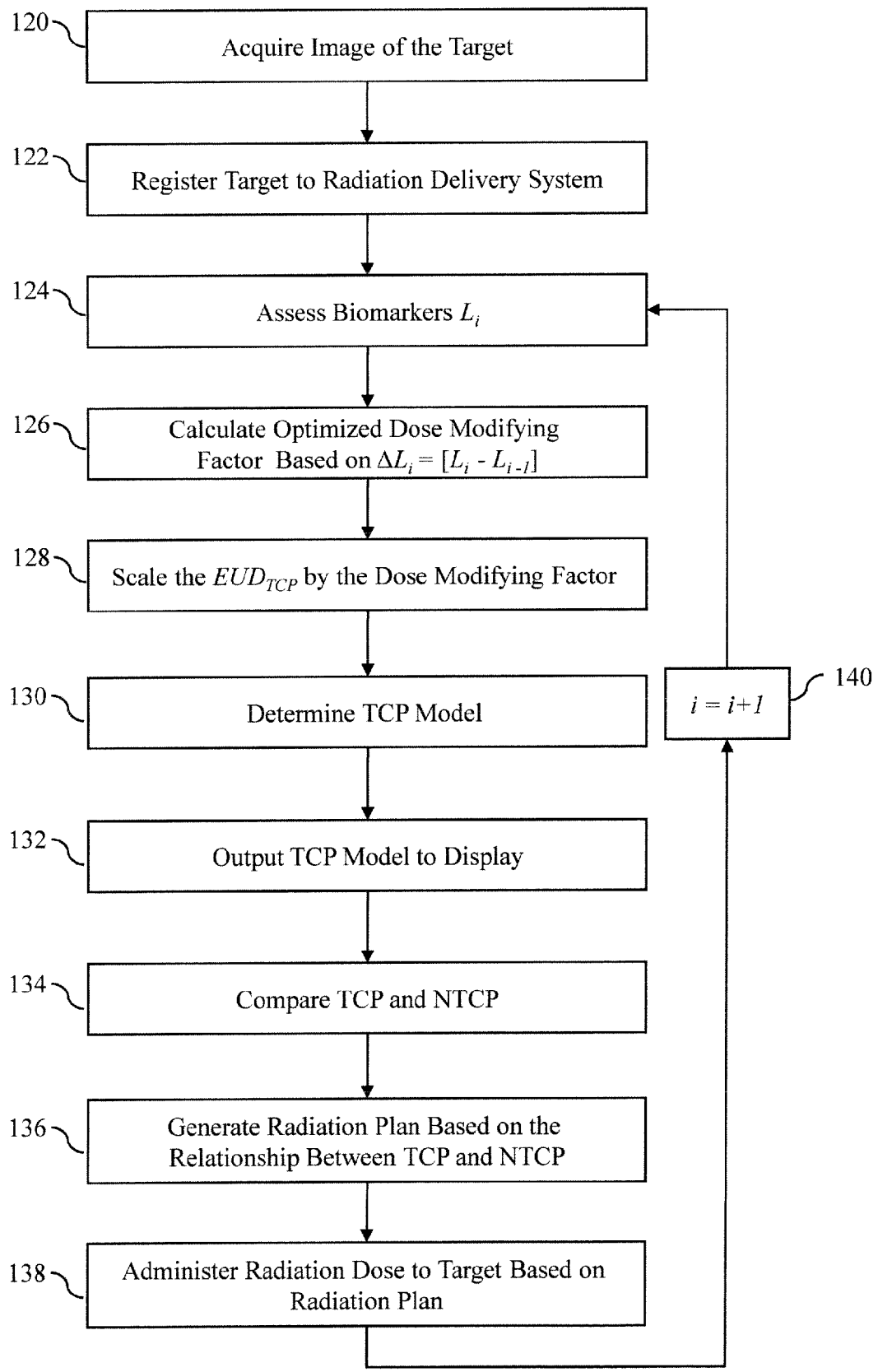
FIG. 3 is a flow diagram of a TCP modeling process.

With continuing reference to FIG. 3, the TCP model is refined in an iterative process in which the optimized dose modifying factor is set as the baseline in subsequent iterations. First a diagnostic image is acquired in step 120 using a CT, MRI, PET, SPECT, or another imaging modality. In step 122, the target is localized in a diagnostic image and then registered with the radiation delivery system 40 using any number of means such as active, passive, or intrinsic anatomical markers. Biomarkers are assessed in step 124. The biomarkers can be measured in vitro, based on patient history, anamnetic data, mass spectrometric protein signatures, and the like. A value is assigned to the individual biomarkers which are then used to calculate the optimized dose modifying factor in step 126. In the first iteration (for i=1), the dose modifying factor is based on an initial baseline because there is no prior dose modifying factor available. The dose modifying factor is then used to weight the $EUD_{TCP}$ model in step 128 in response to the patient specific biomarkers from step 124. The patient specific $EUD_{TCP}$ model is used in the calculation of the TCP model in step 130. The TCP model is then outputted 132 (FIGS. 4 and 5) on the graphic display of console 80 along with the TCP and the NTCP and the TCP are compared as in step 134. The radiation oncologist then determines if optimizations to the radiation therapy plan are needed in step 136. Such adjustments may include adjusting total dose applied, location of the dose, or changing the treatment regime to another such as IMRT, 3D conformal radiotherapy, or another fractionation scheme. In step 138, a radiation dose is administered to the target as prescribed by the optimized radiation plan. The optimized dose modifying factor is set as the baseline in step 140, and the optimization is reiterated until the radiation oncologist can determine that treatment is no longer needed.

Figure 4:
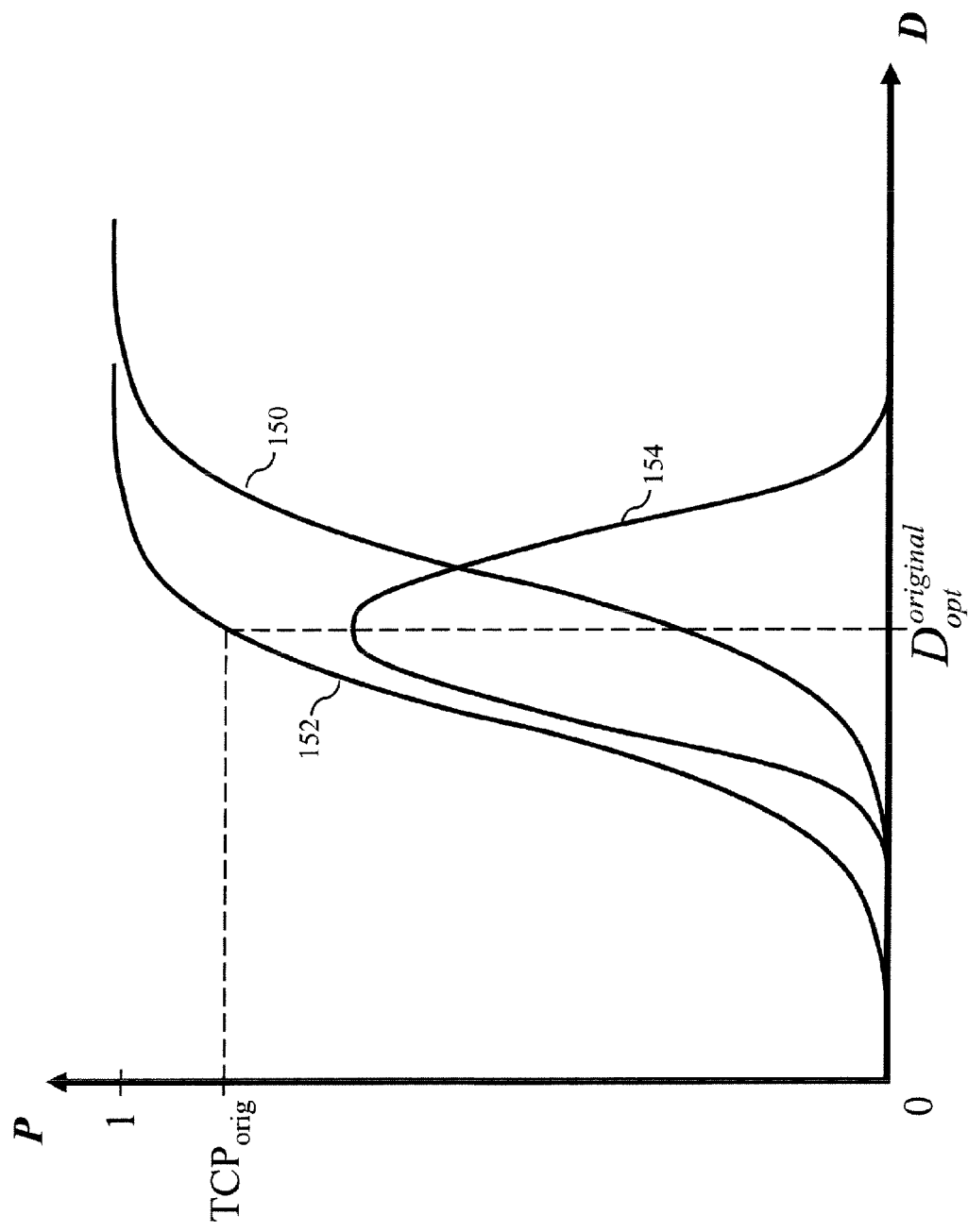
FIG. 4 is a graphical depiction of initial NTCP and TCP models and their difference.
Figure 5:
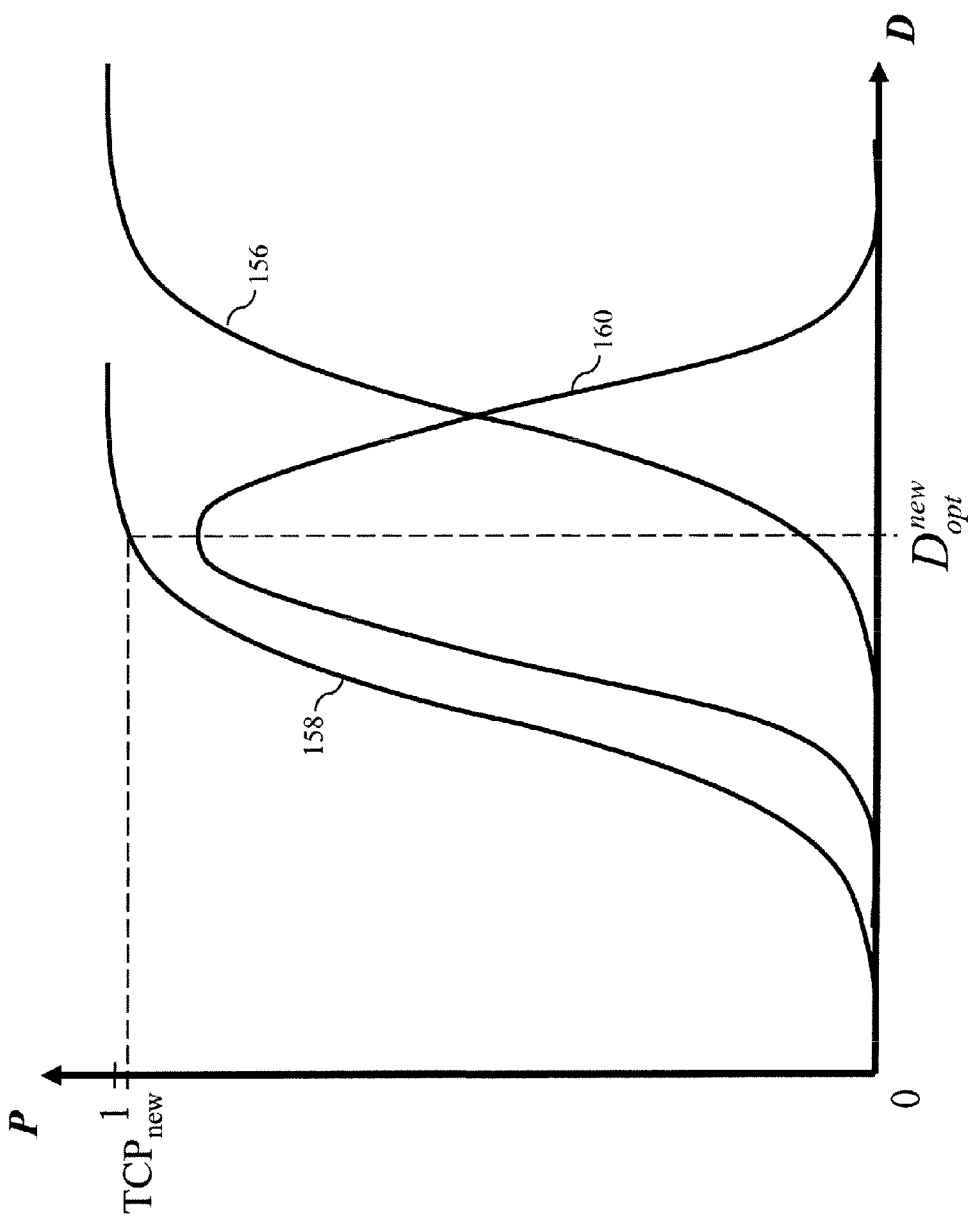
FIG. 5 is a graphical depiction of the NTCP and TCP models after optimization to maximize the difference.
Figure 6:
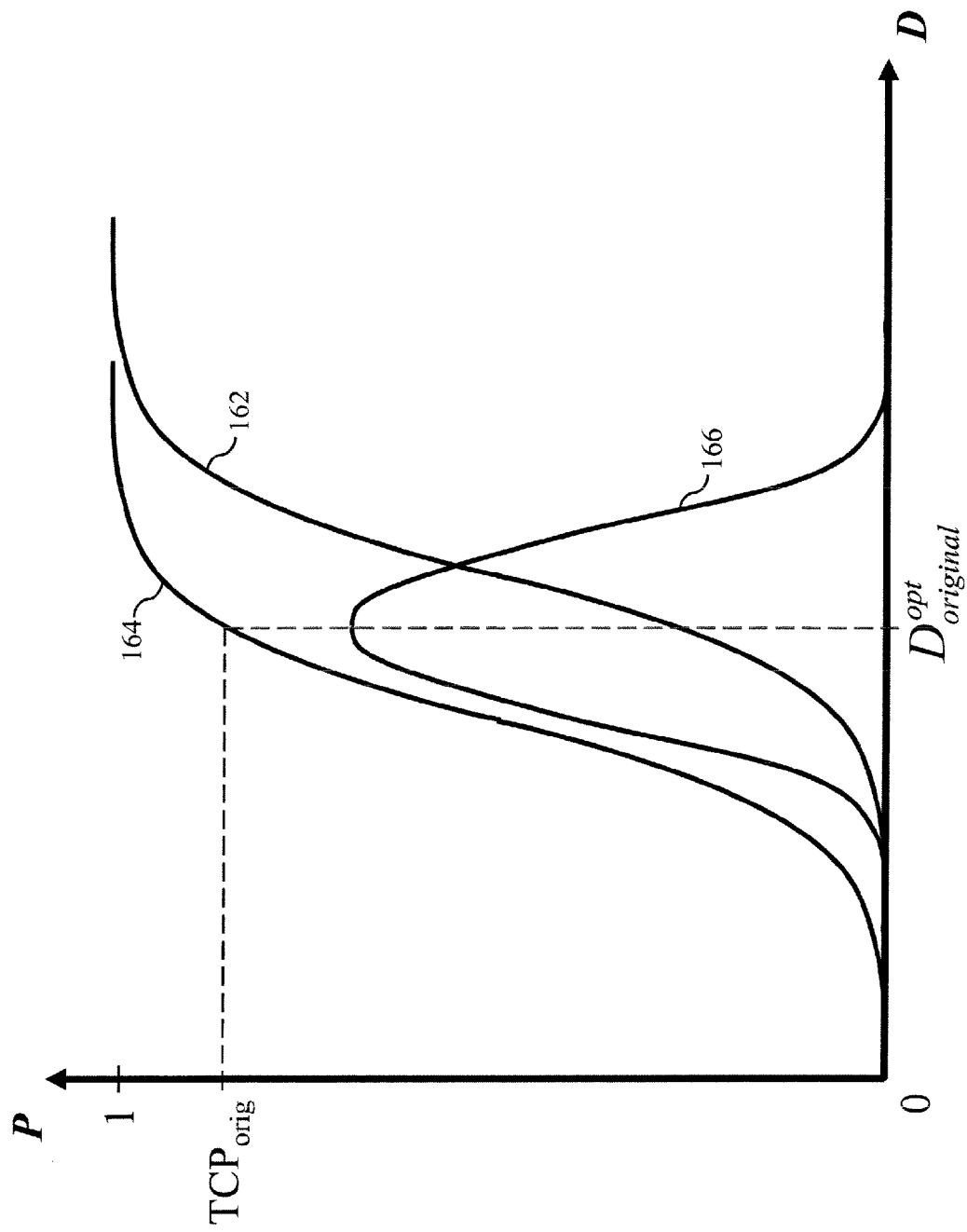
FIG. 6 is a graphical depiction of a further optimization of the NTCP model.

With reference to FIG. 4, an example of a graph of the initial or pretreatment NTCP model 150 and TCP model 152 outputted to the graphical interface of console 80 for inspection by the radiation oncologist. The NTCP model is optimized to maximize the difference 154 between the NTCP and the TCP. The optimized NTCP model, shown in FIG. 5, illustrates an optimized NTCP model 156 in which the TCP 158 is modeled and results in a greater difference 160 between the optimized NTCP model and TCP. The treatment tends to inflame the healthy tissue. During radiotherapy, the NTCP curve is optimized again based on the patient's tissue reactions. In the example of FIG. 6, the previously optimized NTCP is re-optimized with the biomarkers for various surrounding tissues revised for their respective degrees of inflammation to generate a re-optimized NTCP 162, which results in less radiation exposure to the normal tissue while the new TCP 164 is larger than the prior TCP 158 and the difference 166 is smaller which results in increased radiation exposure to diseased tissue as well as the healthy tissue. In this manner, the radiation dose may change from treatment session to treatment session to accommodate treatments induced or other changes to tissue adjacent the target region.

In another embodiment, the patient specific dose modifying factors $g_{NTCP}$ and $g_{TCP}$ are calculated for each voxel or group of voxels. The resulting EUD equations are as follows:

$$EUD = \left( \sum_{i=1}^{N} D_i^{1/n} * \frac{V_i}{V_{tot}} \right)^n \cdot g(M_1, \Delta M_1, M_2, \Delta M_2, \dots ) \quad (3d)$$

$$EUD = \left( \sum_{i=1}^{N} D_i^{1/n} * \frac{V_i}{V_{tot}} \right)^n \cdot g(M_1, \Delta M_1, M_2, \Delta M_2, \dots ) \quad (3e)$$

where $g_i$ and $g_j$ are the dose modifying factors for each subvolume. For example, the EUD can be calculated for a plurality of subvolumes of a region of interest such as the kidney. Furthermore, an image representation can be reconstructed graphically depicting the EUD across the region interest which allows the radiation delivery system to deliver a localized dose.

In another embodiment, a non-iterative patient specific adaptive radiation therapy plan is generated. An initial radiation therapy plan is generated by revising a conventional NTCP model and/or TCP model with at least one measured patient specific biomarker prior to administering a dose of radiation. The conventional NTCP and/or TCP models are generated using known methods in the conventional arts then are mathematically modified by a value associated with the patient specific biomarker. Initial and subsequent doses of radiation are administered based on the initial radiotherapy plan or may be modified in subsequent sessions as described above.

In another embodiment, a conventional radiation therapy plan is generated based on a conventional NTCP and/or TCP model. The conventional NTCP and/or TCP model is generated using known methods in the conventional arts. An initial dose of radiation is administered to the target region based on the conventional radiotherapy plan. A revised radiation therapy plan is generated by modifying the conventional NTCP and/or TCP model based on at least one patient specific biomarker. A value is associated with the patient specific biomarker is used to mathematically modify the conventional NTCP and/or TCP model. The revised radiation therapy plan is refined in an iterative process in which the biomarker is monitored between consecutive radiation doses and the revised NTCP and/or TCP model is updated based on differences between the previous measurement and the current measurement. That is, in a first iteration a conventional NTCP and/or TCP models are used to administer a dose of radiation. In a second iteration, the conventional NTCP and/or TCP models are revised based on at least one measured biomarker and a second dose of radiation is applied based on the revised NTCP and/or TCP models. In subsequent iterations, the revised NTCP and/or TCP models are further refined based on a mathematical relationship between previously measured biomarkers and the current measured biomarkers.

In another embodiment, a conventional radiation therapy plan is generated based on a conventional NTCP and/or TCP model. The conventional NTCP and/or TCP model is generated using known methods in the conventional arts. An initial dose of radiation is administered to the target region based on the conventional radiotherapy plan. Prior to administering the initial dose of radiation, at least one initial biomarker is measured. A revised radiation therapy plan is generated by modifying the conventional NTCP and/or TCP model based on a mathematical relationship between an updated biomarker and the initial biomarker. The revised radiation therapy plan is refined in an iterative process in which the biomarkers are updated between consecutive radiation therapy sessions. Further clarified, in a first iteration a conventional NTCP and/or TCP model is used to administer a dose of radiation and an initial biomarker is generated. In a second iteration, the conventional NTCP and/or TCP model is revised based on a relationship between an updated biomarker and the initial biomarker and a second dose of radiation is applied based on the revised NTCP and/or TCP model. In subsequent iterations, the revised NTCP and/or TCP model is further refined based on a mathematical relationship between previously measured biomarker and the current measured biomarker.

Having thus described the preferred embodiments, the invention is now claimed to be:

1. A method for generating a patient specific therapy plan for a patient, comprising:
   (a) with a processor, generating an initial therapy plan for administering an initial therapy to the patient, wherein the initial therapy plan is generated using at least one of an initial normal tissue complication probability (NTCP) model and an initial tumor control probability (TCP) model of a target region, and wherein the at least one of the NTCP model and the TCP model is adapted to the patient based on a first value of at least one biomarker of the patient;
   (b) administering therapy to the patient using the initial therapy plan with a therapy delivery system;
   (c) with the processor, generating a revised therapy plan for administering a revised therapy to the patient, wherein the revised therapy plan is generated using at least one of an updated NTCP model and an updated TCP model of the target region of the patient, wherein the at least one of the initial NTCP model and the initial TCP model is adapted to the patient based on a second value of the at least one biomarker of the patient; (d) administering therapy to the patient based on the revised therapy plan with the therapy delivery system; and wherein the at least one biomarker of the patient is Hb, CRP, PSA, TNF-α, ferritin, transferrin, LDH, IL-6, hepcidin, creatinine, glucose, HbA1c, DNA end binding complexes (DNA-EBCs), HIF-1α, Galectin-1, CAP43, NDRG1, or telomere length;

wherein at least one patient biomarker is an additional biomarker chosen from in vitro test values, mass spectrometric protein signatures, tumor type, tumor grade, tumor stage, primary tumor site, Gleason score, cologenic assays, previous treatment, previous abdominal surgery, hormonal medication, anticoagulantia medication, age, diabetes, and tumor growth related measures;

wherein the NTCP model includes an EUD model expressed as:

$$EUD = \left(\sum_{i=1}^{N} D_1^{1/n} * \frac{v_i}{v_{tot}}\right)^n \cdot y(M_1, \Delta M_1, M_2, \Delta M_2, \ldots)$$

where EUD is an equivalent uniform dose, $D_i$ is a physical dose to a volume segment $v_i$ of the target region, $v_{tot}$ is a total evaluated organ volume, $\Delta M_1$, $\Delta M_2$, . . . are a difference between a first and second set of biomarkers, N is the number of volume segments $v_i$, $M_1$ is a baseline value of a first biomarker, $M_2$ is a baseline value of a second biomarker and g is a scalar evaluated based on the first and second sets of biomarkers and the difference between the first and second sets of biomarkers, and n varies between 0 for a maximum dose and 1 for a minimum dose; and the TCP model includes an EUD model expressed as:

$$EUD = \left(\sum_{i=1}^{N} D_j^{1/n} * \frac{v_j}{v_{tot}}\right)^n * g(L_1, \Delta L_1, L_2, \Delta L_2 \ldots)$$

where EUD is an equivalent uniform dose, $D_j$ is a physical dose to a volume $v_j$ of the target region, N is the number of volume segments $v_j$, $v_{tot}$ is a total evaluated organ volume, $L_1$, $L_2$ are baseline values associated with a first and second cancerous tissue, $\Delta L_1$, $\Delta L_2$, . . . are a difference between the first and second sets of biomarkers, and g is a scalar evaluated based on the first and second sets of biomarkers and the difference between the first and second sets of biomarkers, and n varies between 0 for a maximum dose and 1 for a minimum dose.

2. The method according to claim 1, further including:
   (d) administering the revised therapy to the patient based on the revised therapy plan with the therapy delivery system.

3. The method according to claim 1, wherein the at least one patient biomarker is associated with at least one of sensitivity of healthy tissue and cancerous tissue to the therapy and further including:
   associating one of the first value and the second value with the at least one patient biomarker.

4. The method according to claim 1, wherein the scalar value is a dose modifying factor and the method further includes:

initially setting the dose modifying factor prior to treatment; and modifying the dose modifying factor based on a mathematical relationship between the first value and the second value of the at least one biomarker generated in steps (a) and (c).

5. The method according to claim 2, further including:
acquiring an image of the target region with a diagnostic imaging system;
segmenting the target region with the processor;
determining the NTCP model with the processor;
determining the TCP model with the processor;
registering the target region in a diagnostic image to the therapy delivery system;
performing steps (a)-(d);
re-registering the target region; and
repeating steps (c)-(d) after therapy has been administered to the patient based on the revised therapy plan.

6. A non-transitory computer readable medium carrying a program which controls a processor to perform the method according to claim 1.

7. An apparatus comprising:
a processor configured to:
determine at least a first normal tissue complication probability (NTCP) model of a target region based on a first set of patient specific biomarkers;
generate an initial therapy plan for administering an initial therapy to the patient, wherein the initial therapy plan is generated using the first NTCP model, wherein the first NTCP model is adapted based on a value of the first set of patient specific biomarkers; and
a therapy delivery system configured to:
deliver therapy to the patient using the initial therapy plan;
wherein the processor is further configured to:
determine a second NTCP model of the target region based on a second set of patient specific biomarkers; and
generate a revised therapy plan for administering a revised therapy to the patient, wherein the revised therapy plan is generated using the second NTCP model, wherein the second NTCP model is determined by:

$$NTCP = \frac{1}{\sqrt{2\pi}} \int_{-\infty}^{t} \exp\left(\frac{-x^2}{2}\right) dx$$

where, $$t = \frac{EUD - TD_Z}{m * TD_Z}$$

where, $$EUD = \left(\sum_{i=1}^{N} D_i^{1/n} * \frac{V_i}{V_{tot}}\right)^n \cdot g(M_1, \Delta M_1, M_2, \Delta M_2, \ldots)$$

where EUD is an equivalent uniform dose, $TD_Z$ is a dose that provides a Z % chance of a risk complication, $D_i$ is a physical dose to a volume segment $v_i$ of the target region, $v_{tot}$ is a total evaluated organ volume, $\Delta M_1$, $\Delta M_2$, ... are a difference between the first and second sets of biomarkers, N is the number of volume segments $v_i$, m is the slope of the NTCP curve, $M_1$ is a baseline value of a first biomarker, $M_2$ is a baseline value of a second biomarker and g is a scalar evaluated based on the first and second sets of biomarkers and the difference between the first and second sets of biomarkers, and n varies between 0 for a maximum dose and 1 for a minimum dose; and wherein the therapy delivery system is further configured to administer therapy to the patient based on the revised therapy plan.

8. A method comprising:
(a) determining a first set of patient specific biomarkers of a patient and determining at least a first tumor control probability (TCP) model of a target region based on a first set of biomarkers $L_1$;
(b) with a processor, generating an initial therapy plan for administering an initial radiation therapy to the patient, wherein the initial therapy plan is generated using at least the first TCP model, wherein the first TCP model is adapted based on a value of the first set of patient specific biomarkers;
(c) administering radiation therapy to the patient with a radiation therapy delivery system comprising a therapeutic radiation source configured to deliver therapeutic radiation to the patient in accordance with the initial therapy plan;
(d) determining a second set of patient specific biomarkers $L_2$ of a patient and determining a second TCP model of the target region based on the second set of biomarkers; and
(e) generating a revised therapy plan for administering a revised therapy to the patient, wherein the revised therapy plan is generated using at least the second TCP model, wherein the second TCP model is determined by:

$$TCP = \frac{1}{\sqrt{2\pi}} \int_{-\infty}^{t} \exp\left(\frac{-x^2}{2}\right) dx$$

where, $$t = \frac{EUD - TD_Z}{m * TD_Z}$$

where, $$EUD = \left(\sum_{i=1}^{N} D_1^{1/n} * \frac{v_j}{v_{tot}}\right)^n * g(L_1, \Delta L_1, L_2, \Delta L_2 \ldots)$$

where EUD is an equivalent uniform dose, $TD_Z$ is a dose that provides a Z % chance of a risk complication, $D_j$ is a physical dose to a volume $v_j$ of the target region, $v_{tot}$ is a total evaluated organ volume, $L_1$, $L_2$ are baseline values associated with a first and second cancerous tissue, $\Delta L_1$, $\Delta L_2$, ... are a difference between the first and second sets of biomarkers, N is the number of volume segments $v_j$, m is the slope of the TCP curve, and g is a scalar evaluated based on the first and second sets of biomarkers and the difference between the first and second sets of biomarkers, and n varies between 0 for a maximum dose and 1 for a minimum dose; and
(f) administering radiation therapy to the patient with the radiation therapy delivery system.

9. A method for generating a patient specific treatment plan, comprising:
(a) determining a first set of patient specific biomarkers;
(b) with the processor, generating an initial treatment plan using at least one of a first normal tissue complication probability (NTCP) model and a first tumor control probability (TCP) model of a target region, wherein the at least one of the first NTCP model and the first TCP model is adapted based on a value of the first set of patient specific biomarkers $M_1$;

(c) administering a first therapy to the target region based on the initial treatment plan with a radiation delivery device;

(d) determining a second set of patient specific biomarkers $M_2$;

(e) with the processor, generating a revised treatment plan using at least one of a second NTCP model and second TCP model of the target region, wherein the at least one of the second NTCP model and the second TCP model is adapted based on a value of the second set of patient specific biomarkers, wherein at least one of the second NTCP model and the second TCP model are expressed in terms of an equivalent uniform dose (EUD) function where $$EUD = \left(\sum_{i=1}^{N} D_i^{1/n} * \frac{v_i}{v_{tot}}\right)^n \cdot g(M_1, \Delta M_1, M_2, \Delta M_2, \ldots),$$

wherein $D_i$ is a physical dose to a volume segment $v_i$ of the target region, $v_{tot}$ is a total evaluated organ volume, $M_1$ is a baseline value of a first biomarker, $M_2$ is a baseline value of a second biomarker, $\Delta M_1$, $\Delta M_2$, ... are a difference between the first and second sets of biomarkers, N is the number of volume segments $v_i$, and g is a scalar evaluated based on the first and second sets of biomarkers and the difference between the first and second sets of biomarkers, and n varies between 0 for a maximum dose and 1 for a minimum dose;

(f) with the radiation delivery device, administering a second therapy to the target region based on the second NTCP model and the second TCP model; and (g) repeating the steps (d)-(f) to further revise the second NTCP model and the second TCP model for a subsequent treatment session;

wherein the processor integrates individual patent specific information derived from a single or plurality of biomarkers.

10. The method according to claim 9, wherein the first set of patient specific biomarkers and the second set of patient specific biomarkers are mutually exclusive.

11. A processor configured to perform the steps of:

(a) receiving a first set of patient specific biomarkers;

(b) generating an initial therapy plan using at least one of a first normal tissue complication probability (NTCP) model and a first tumor control probability (TCP) model of a target region based on the first set of biomarkers;

(c) controlling a therapy delivery device to deliver therapy to the target based on the initial therapy plan;

(d) receiving a second set of patient specific biomarkers; and (e) generating a revised therapy plan using at least one of a second NTCP model and a second TCP model of the target region based on differences between the first and second set of biomarkers $\Delta M_1$ and $\Delta M_2$; wherein the revised therapy plan is configured to control the therapy delivery device to deliver an optimized dose of therapy to the target;

wherein each NTCP model includes an EUD model expressed as:

$$EUD = \left(\sum_{i=1}^{N} D_i^{1/n} * \frac{v_i}{v_{tot}}\right)^n \cdot g(M_1, \Delta M_1, M_2, \Delta M_2, \ldots)$$

where EUD is an equivalent uniform dose, $D_i$ is a physical dose to a volume segment $v_i$ of the target region, $v_{tot}$ is a total evaluated organ volume, $\Delta M_1$, $\Delta M_2$, ... are a difference between the first and second sets of biomarkers, N is the number of volume segments $v_i$, $M_1$ is a baseline value of a first biomarker, $M_2$ is a baseline value of a second biomarker and g is a scalar evaluated based on the first and second sets of biomarkers and the difference between the first and second sets of biomarkers, and n varies between 0 for a maximum dose and 1 for a minimum dose; and the TCP model includes an EUD model expressed as:

$$EUD = \left(\sum_{i=1}^{N} D_j^{1/n} * \frac{v_j}{v_{tot}}\right)^n * g(L_1, \Delta L_1, L_2, \Delta L_2 \ldots)$$

where EUD is an equivalent uniform dose, $D_j$ is a physical dose to a volume $v_j$ of the target region, N is the number of volume segments $v_i$, $v_{tot}$ is a total evaluated organ volume, $L_1$, $L_2$ are baseline values associated with a first and second cancerous tissue, $\Delta L_1$, $\Delta L_2$, ... are a difference between the first and second sets of biomarkers, and g is a scalar evaluated based on the first and second sets of biomarkers and the difference between the first and second sets of biomarkers, and n varies between 0 for a maximum dose and 1 for a minimum dose;

wherein the processor integrates individual patent specific information derived from a single or plurality of biomarkers.

12. The processor according to claim 11, wherein the processor is further configured to evaluate in vitro test values that are cellular, proteomic, or genetic in origin, wherein the in vitro tests include at least one of Hb, CRP, PSA, TNF-α, ferritin, transferrin, LDH, IL-6, hepcidin, creatinine, glucose, HbA1c, DNA end binding complexes (DNA-EBCs), HIF-1α, Galectin-1, CAP43, NDRG1, and telomere length.

13. The processor according to claim 11 wherein at least one of the second NTCP and TCP models are expressed as:

$$\frac{1}{\sqrt{2\pi}} \int_{-\infty}^{t} \exp\left(\frac{-x^2}{2}\right) dx$$

where, $$t = \frac{EUD - TD_Z}{m * TD_Z}$$

where, $$EUD = \left(\sum_{i=1}^{N} D_i^{1/n} * \frac{v_i}{v_{tot}}\right)^n \cdot g(M_1, \Delta M_1, M_2, \Delta M_2, \ldots)$$

where EUD is an equivalent uniform dose, $TD_Z$ is a dose that provides a Z % chance of a risk complication, $D_i$ is a physical dose to a volume segment $v_i$ of the target region, $v_{tot}$ is a total evaluated organ volume, $M_1$ is a baseline value of a first biomarker, $M_2$ is a baseline value of a second biomarker, $\Delta M_1$, $\Delta M_2$, ... are a difference between the first and second sets of biomarkers, N is the number of volume segments $v_i$, m is the slope of the NTCP curve, and g is a scalar evaluated based on the first and second sets of biomarkers and the difference between the first and second sets of biomarkers, and n varies between 0 for a maximum dose and 1 for a minimum dose.

14. A system comprising:
a therapy delivery apparatus configured to delivery therapy to a target region; and
a processor configured to perform the steps of:
(a) determining at least one of a first normal tissue complication probability (NTCP) model and a first tumor control probability (TCP) model of the target region;
(b) controlling the therapy delivery device to deliver therapy to conduct a first therapy session to the target region with a protocol based on at least one of the first NTCP model and first TCP model;
(c) determining or updating a set of patient specific biomarkers;
(d) updating at least one of the first NTCP model and the first TCP model of the target region based on the set of biomarkers;
(e) controlling the therapy delivery device to conduct a second therapy session to the target region based on at least one of the updated NTCP model and TCP model; and
(f) repeating the steps (c)-(e) to further revise the NTCP model for a subsequent treatment session;
wherein the NTCP model includes an EUD model expressed as:

$$EUD = \left(\sum_{i=1}^{N} D_i^{1/n} * \frac{v_i}{v_{tot}}\right)^n \cdot g(M_1, \Delta M_1, M_2, \Delta M_2, \ldots)$$

where EUD is an equivalent uniform dose, $D_i$ is a physical dose to a volume segment $v_i$ of the target region, $v_{tot}$ is a total evaluated organ volume, $\Delta M_1, \Delta M_2, \ldots$ are a difference between a first and second sets of biomarkers, N is the number of volume segments $v_i$, $M_1$ is a baseline value of a first biomarker, $M_2$ is a baseline value of a second biomarker and g is a scalar evaluated based on the first and second sets of biomarkers and the difference between the first and second sets of biomarkers, and n varies between 0 for a maximum dose and 1 for a minimum dose; and the TCP model includes an EUD model expressed as:

$$EUD = \left(\sum_{i=1}^{N} D_j^{1/n} * \frac{v_j}{v_{tot}}\right)^n * g(L_1, \Delta L_1, L_2, \Delta L_2 \ldots)$$

where EUD is an equivalent uniform dose, $D_j$ is a physical dose to a volume segment $v_j$ of the target region, N is the number of volume segments $v_j$, $v_{tot}$ is a total evaluated organ volume, $L_1, L_2$ are baseline values associated with a first and second cancerous tissue, $\Delta L_1, \Delta L_2, \ldots$ are a difference between the first and second sets of biomarkers, and g is a scalar evaluated based on the first and second sets of biomarkers and the difference between the first and second sets of biomarkers, and n varies between 0 for a maximum dose and 1 for a minimum dose.

15. The system according to claim 14, wherein the processor is further configured to
performing in vitro tests to determine evaluate in vitro test values that are cellular, proteomic, or genetic in origin, wherein the in vitro tests include at least one of Hb, CRP, PSA, TNF-α, ferritin, transferrin, LDH, IL-6, hepcidin, creatinine, glucose, HbA1c, DNA end binding complexes (DNA-EBCs), HIF-1α, Galectin-1, CAP43, NDRG1, and telomere length.

16. The system according to claim 14 wherein at least one of the updated NTCP and TCP models are expressed as:

$$\frac{1}{\sqrt{2\pi}} \int_{\infty}^{t} \exp\left(\frac{-x^2}{2}\right) dx$$

where, $$t = \frac{EUD - TD_Z}{m * TD_Z}$$

where, $$EUD = \left(\sum_{i=1}^{N} D_i^{1/n} * \frac{v_i}{v_{tot}}\right)^n \cdot g(M_1, \Delta M_1, M_2, \Delta M_2, \ldots)$$

where EUD is an equivalent uniform dose, $TD_Z$ is a dose that provides a Z % chance of a risk complication, $D_i$ is a physical dose to a volume segment $v_i$ of the target region, $v_{tot}$ is a total evaluated organ volume, $M_1$ is a baseline value of a first biomarker, $M_2$ is a baseline value of a second biomarker, $\Delta M_1, \Delta M_2, \ldots$ are a difference between the first and second sets of biomarkers, N is the number of volume segments $v_i$, m is the slope of the NTCP curve, and g is a scalar evaluated based on the first and second sets of biomarkers and the difference between the first and second sets of biomarkers, and n varies between 0 for a maximum dose and 1 for a minimum dose.

* * * * *